United States Patent
Tanto et al.

(10) Patent No.: US 8,692,029 B2
(45) Date of Patent: Apr. 8, 2014

(54) METHOD AND DEVICE FOR SYNTHESIZING ACROLEIN

(75) Inventors: Masashi Tanto, Tokyo (JP); Yasunari Sase, Tokyo (JP); Hiroyuki Ito, Tokyo (JP); Toshiaki Matsuo, Hitachi (JP); Takeyuki Kondo, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/380,271

(22) PCT Filed: Jun. 30, 2010

(86) PCT No.: PCT/JP2010/061145
§ 371 (c)(1),
(2), (4) Date: Dec. 22, 2011

(87) PCT Pub. No.: WO2011/002023
PCT Pub. Date: Jan. 6, 2011

(65) Prior Publication Data
US 2012/0095269 A1    Apr. 19, 2012

(30) Foreign Application Priority Data
Jul. 1, 2009  (JP) ................ 2009-157090

(51) Int. Cl.
*C07C 45/42* (2006.01)
*B01J 19/00* (2006.01)

(52) U.S. Cl.
USPC .......................... 568/486; 422/119

(58) Field of Classification Search
USPC .......................... 568/486; 422/119
See application file for complete search history.

(56) References Cited

FOREIGN PATENT DOCUMENTS

| | | |
|---|---|---|
| EP | 2 186 790 A1 | 5/2010 |
| JP | 3934630 | 3/2007 |
| JP | 4052748 | 12/2007 |
| JP | 2009-57289 | 3/2009 |
| JP | 2009-132663 | 6/2009 |
| WO | WO 2008/061860 A1 | 5/2008 |

OTHER PUBLICATIONS

Kusdiana et al. Kinetics of transesterifcation in rapeseed oil to biodiesel fuel as treacted in supercritical methanol. Fuel, 2001, vol. 80, pp. 693-698.*
Masaru Watanabe, et al., Acrolein Synthesis from Glycerol in Hot-Compressed Water, Bioresource Technology 98, 2007, pp. 1285-1290.
Kondo, et al. The 74th Annual Meeting Abstracts J108, (2009), the Society of Chemical Engineers, Japan with the English translation of relevant portion.

* cited by examiner

*Primary Examiner* — Sikarl Witherspoon
(74) *Attorney, Agent, or Firm* — Antonelli, Terry, Stout & Kraus, LLP.

(57) ABSTRACT

An object of the present invention is to provide an industrially applicable method for producing acrolein via treatment with supercritical water from glycerin obtained as a by-product during the process of biodiesel fuel production from waste animal/plant fat or oil with the use of an alkali catalyst.
The present invention provides a method for producing acrolein, which comprises: a determination step of determining the hydrogen ion concentration in glycerin obtained as a by-product; an acid addition step of adding to the glycerin an acid at an amount calculated based on the results of the determination step so as to make the glycerin acidic; and a supercritical water treatment step of allowing supercritical water to act on the glycerin after the acid addition so as to produce acrolein from the glycerin.

13 Claims, 4 Drawing Sheets

METHOD AND DEVICE FOR SYNTHESIZING ACROLEIN

TECHNICAL FIELD

The present invention relates to a method and a device for synthesizing acrolein from glycerin obtained as a by-product upon production of fatty acid methyl ester (biodiesel fuel) from waste fat or oil.

BACKGROUND ART

In recent years, carbon-neutral biodiesel fuel has been gaining attention as a diesel engine fuel. A known method for obtaining biodiesel comprises: carrying out a transesterification reaction of monohydric alcohol and triglyceride contained in a raw material such as a plant oil, animal oil, or waste plant or animal oil; and removing glycerin formed as a by-product (Chemical formula 1). In the reaction of Chemical formula 1, biodiesel is obtained in the form of an ester of low viscous monohydric alcohol and fatty acid. Such ester can be used as a fuel.

Glycerin obtained as a by-product upon biodiesel production also contains a catalyst, unesterified fatty acid, and the like. Such glycerin cannot be effectively used and thus it is discarded under present circumstances. Therefore, effective use of glycerin obtained as a by-product is a recent object in the art.

[Chemical formula 1]

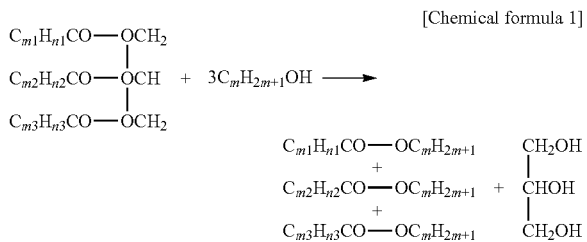

In general, glycerin is used as a raw material for producing nitroglycerin, pharmaceutical products, cosmetics, sweeteners, and the like. However, in any case, high-purity glycerin is necessary, while on the other hand, there is no large demand for glycerin production. For such reasons, it is impossible to sell glycerin purified from glycerin obtained as a by-product upon biodiesel production given the prices in view of the purification cost and the amount of purified glycerin under present circumstances.

Patent Document 1 describes a biodiesel production method wherein glycerin obtained as a by-product is purified via distillation or the like. However, the method described in Patent Document 1 comprises a step of purifying glycerin, resulting in additional cost increase. In this regard, it is difficult to achieve excellent economic efficiency. Further, it is not always possible to obtain high-purity glycerin with the method. Therefore, it would be highly probable that the method would be inappropriate for commercial use.

Patent Document 2 describes a method for producing biodiesel and glycerin using high-temperature methanol at about its critical temperature without an alkali catalyst. In this method, there is no need to use an alkali or a neutralizer that becomes an impurity, facilitating purification of biodiesel and glycerin. However, this production method requires much greater energy than the alkali catalyst method. The method is too costly to produce less expensive materials, which is problematic.

In addition to the production methods described in Patent Documents 1 and 2, there are known methods for obtaining high-purity glycerin via an enzyme method, a supercritical method, and the like. However, all of the above production methods cause cost increase, making it difficult to achieve excellent economic efficiency. Therefore, it is difficult to use such methods for industrial applications.

Meanwhile, when glycerin is used as a chemical, it is used as a raw material for producing acrolein, which is a raw material for acrylic acid, 1,3-propanediol, or the like.

Non-Patent Document 1 describes a method for producing acrolein by adding sulfuric acid to glycerin and treating the resultant with supercritical water. According to this method, acrolein can be obtained from glycerin at a yield of 70% or more because of the high catalyst activity of protons in supercritical water.

[Chemical formula 2]

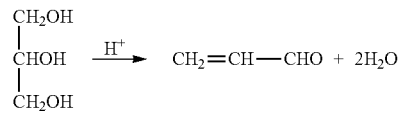

In Non-Patent Document 1, the method is merely examined under conditions comprising a glycerin concentration in a reaction mixture subjected to a supercritical reaction of as low as approximately 1.0%. However, for industrial applications, highly concentrated glycerin must be used as a raw material in consideration of efficient use of energy for preparation of supercritical water.

Non-Patent Document 2 describes a method for synthesizing acrolein from glycerin via treatment with an acid and supercritical water. According to the method, in order to maintain the raw material yield at a high level for acrolein synthesis even at a high glycerin concentration, it is necessary to set the reaction time and the catalyst aid (acid) concentration at levels appropriate for high glycerin concentrations. According to Non-Patent Document 2, it is desirable that the relation between the glycerin concentration in a reaction mixture subjected to a supercritical reaction ($[G]_R$) and the hydrogen ion concentration ($[H^+]_R$) expressed by the following equation be satisfied: $[H^+]_R{}^2/[G]_R$=15 to 25 mM²/wt % (and particularly desirably 18 to 22 mM²/wt %). If the above relation between the glycerin concentration and the hydrogen ion concentration does not fall within the above ranges (that is to say, if the acid concentration is excessively low or high), by-products such as tar and carbon are increasingly produced, resulting in reduction of raw material yield. Further, such by-products might cause a risk of obstruction in a reactor or pipes. This might interrupt stable plant operation.

CITATION LIST

Patent Document

Patent Document 1: JP Patent No. 3934630
Patent Document 2: JP Patent No. 4052748

Non-Patent Document

Non-Patent Document 1: M. Watanabe et al., Bioresource Technology 98 (2007)1285-1290
Non-Patent Document 2: Kondo et al., the 74th Annual Meeting Abstracts J108 (2009), the Society of Chemical Engineers, Japan

SUMMARY OF INVENTION

Technical Problem

It is preferable to use, as a raw material for triglyceride used for biodiesel fuel production, waste animal/plant fat or oil that has been disposed of by the food industry and general households. However, waste animal/plant fat or oil contain impurities (e.g., water) generated during cooking. The amounts of such impurities contained in the waste are unstable. Therefore, water and the like are contained at unstable amounts in glycerin obtained as a by-product upon biodiesel production using waste animal/plant fat or oil as a raw material for triglyceride.

As described above with reference to Non-Patent Document 2, it is necessary to precisely control the glycerin concentration and the hydrogen ion concentration in order to reduce by-products such as tar and carbon during a reaction to convert glycerin to acrolein via treatment with supercritical water and an acid. For such reason, it is difficult to apply the conversion reaction for acrolein production using glycerin obtained from waste animal/plant fat or oil.

In addition, when an alkali catalyst is used as a catalyst for biodiesel fuel production, glycerin obtained as a by-product contains the alkali catalyst. In such case, the alkali catalyst forms a salt with the addition of an acid to glycerin obtained as a by-product, which is problematic. In addition, it is difficult to remove the salt formed in glycerin.

Therefore, an object of the present invention is to provide an industrially applicable method for producing acrolein via treatment with supercritical water from glycerin obtained as a by-product during the process of biodiesel fuel production from waste animal/plant fat or oil with the use of an alkali catalyst.

Solution to Problem

As a result of intensive studies in order to achieve the above object, the present inventors have established a method whereby acrolein can be synthesized without any specific process of increasing glycerin purity. The method comprises: determining the hydrogen ion concentration in glycerin obtained as a by-product in a biodiesel extraction step, adding an acid to appropriately adjust the acid concentration; mixing the resultant; and causing the mixture to react with supercritical water so as to cause a dehydration reaction to convert glycerin to acrolein.

Specifically, the present invention encompasses the following inventions.

(1) A method for producing acrolein, wherein acrolein is produced by allowing supercritical water to act on glycerin separated from a mixture containing glycerin and an ester of monohydric alcohol and fatty acid, wherein the mixture is obtained via transesterification of monohydric alcohol and waste fat or oil containing as a main component an ester of fatty acid and glycerin in the presence of an alkali catalyst, the method comprising:

a determination step of determining the hydrogen ion concentration in glycerin;

an acid addition step of adding to the glycerin an acid at an amount calculated based on the results of the determination step so as to make the glycerin acidic; and a supercritical water treatment step of allowing supercritical water to act on the glycerin after the acid addition so as to produce acrolein from the glycerin.

(2) The method according to (1), wherein the alkali catalyst is an oxide or hydroxide of an alkali metal or alkaline-earth metal.

(3) The method according to (1) or (2), which further comprises a precipitate removal step of causing a precipitate of a salt formed from the alkali catalyst and the acid in the glycerin after glycerin neutralization in the acid addition step or after the end of the step and before the start of the supercritical water treatment step so as to separate and remove the precipitate.

(4) The method according to (3), wherein the moisture content in glycerin that is subjected to the precipitate removal step is lower than the stoichiometric quantity of water that allows hydration of the total amount of the salt in the glycerin.

(5) The method according to (4), which further comprises a moisture adjustment step of cooling glycerin and/or removing moisture so as to achieve the moisture content in glycerin that is subjected to the precipitate removal step as defined in (4).

(6) The method according to any one of (1) to (5), which further comprises: a step of adding water used in the supercritical water treatment step at a pressure below the critical pressure of water to glycerin after the acid addition step or during the precipitate removal step if the precipitate removal step is carried out; and a step of adding water used in the supercritical water treatment step at a pressure above the critical pressure of water to the glycerin (7) A method for producing acrolein, wherein acrolein is produced by allowing high-temperature and high-pressure water to act on glycerin separated from a mixture containing glycerin and an ester of monohydric alcohol and fatty acid, wherein the mixture is obtained via transesterification of monohydric alcohol and waste fat or oil containing as a main component an ester of fatty acid and glycerin in the presence of an alkali catalyst, the method comprising:

a determination step of determining the hydrogen ion concentration in glycerin;

an acid addition step of adding to the glycerin an acid at an amount calculated based on the results of the determination step so as to make the glycerin acidic; and;

a high-temperature and high-pressure treatment step of adding water to the glycerin after the acid addition and treating the obtained mixture under high-temperature and high-pressure conditions so as to produce acrolein from the glycerin.

(8) The method according to (7), wherein the high-temperature and high-pressure treatment step is a step of treating the mixture of the glycerin to which the acid has been added and water by adjusting the water temperature to 374° C. or more and the water pressure to 22.06 MPa or more in the mixture.

(9) The method according to (7) or (8), wherein the alkali catalyst is an oxide or hydroxide of an alkali metal or alkaline-earth metal.

(10) The method according to any one of (7) to (9), which further comprises a precipitate removal step of causing a precipitate of a salt formed from the alkali catalyst and the acid in the glycerin after glycerin neutralization in the acid addition step or after the end of the step and before the start of the high-temperature and high-pressure treatment step so as to separate and remove the precipitate.

(11) The method according to (10), wherein the moisture content in glycerin that is subjected to the precipitate removal step is lower than the stoichiometric quantity of water that allows hydration of the total amount of the salt in the glycerin.

(12) The method according to (11), which further comprises a moisture adjustment step of cooling glycerin and/or removing moisture so as to achieve the moisture content in glycerin that is subjected to the precipitate removal step as defined in (11).

(13) The method according to any one of (7) to (12), which further comprises: a step of adding water used in the high-temperature and high-pressure water treatment step at a pressure below the critical pressure of water to glycerin after the acid addition step or during the precipitate removal step if the precipitate removal step is carried out; and a step of adding water used in the high-temperature and high-pressure water treatment step at a pressure above the critical pressure of water to the glycerin

(14) A device for producing acrolein by allowing supercritical water to act on glycerin, which comprises:

a means for determining the hydrogen ion concentration in glycerin used as a raw material;

an acid addition tank for adding an acid to the glycerin used as a raw material provided with a means for supplying the glycerin, a means for supplying the acid, and an agitation means; and a supercritical water treatment means for allowing supercritical water to act on glycerin supplied from the acid addition tank, which is located downstream of the acid addition tank.

(15) The device according to (14), which further comprises a precipitate removal means for separating and removing a precipitate in glycerin supplied from the acid addition tank and supplying the glycerin from which the precipitate has been removed to the supercritical water treatment means, the precipitate removal means being arranged downstream of the acid addition tank and upstream of the supercritical water treatment means.

(16) The device according to (15), which further comprises a water addition tank for adding water to glycerin from which the precipitate has been removed provided with a means for supplying the glycerin from the precipitate removal means, a means for supplying water, and an agitation means, the tank being arranged downstream of the precipitate removal means and upstream of the supercritical water treatment means, and wherein glycerin to which water has been added in the water addition tank is supplied to the supercritical water treatment means.

(17) A device for producing acrolein by allowing high-temperature and high-pressure water to act on glycerin, which comprises:

a means for determining the hydrogen ion concentration in glycerin used as a raw material;

an acid addition tank for adding an acid to the glycerin used as a raw material provided with a means for supplying the glycerin, a means for supplying the acid, and an agitation means; and a high-temperature and high-pressure water treatment means for allowing high-temperature and high-pressure water to act on glycerin supplied from the acid addition tank, which is located downstream of the acid addition tank.

(18) The device according to (17), which further comprises a precipitate removal means for separating and removing a precipitate in glycerin supplied from the acid addition tank and supplying the glycerin from which the precipitate has been removed to the high-temperature and high-pressure water treatment means, the precipitate removal means being arranged downstream of the acid addition tank and upstream of the high-temperature and high-pressure water treatment means.

(19) The device according to (18), which further comprises a water addition tank for adding water to glycerin from which the precipitate has been removed provided with a means for supplying the glycerin from the precipitate removal means, a means for supplying water, and an agitation means, the tank being arranged downstream of the precipitate removal means and upstream of the high-temperature and high-pressure water treatment means, and wherein glycerin to which water has been added in the water addition tank is supplied to the high-temperature and high-pressure water treatment means.

Crude acrolein obtained using the method and the device of the present invention has a low boiling point and thus it can be readily purified. After purification, the obtained acrolein can be used as a raw material for producing acrolein derivatives such as acrylic acid, 1,3-propanediol, and methionine.

Acrylic acid can be readily obtained by oxidizing acrolein in the air. 1,3-propanediol can be obtained via hydrogenation of 3-hydroxypropionaldehyde, which is obtainable by hydrating acrolein, in the presence of a catalyst such as Pt or Ni. Methionine can be obtained by producing 3-methylmercaptopropionaldehyde via Michael addition of acrolein with methyl mercaptan, and then reacting the product with hydrogen cyanide, ammonia, and carbon dioxide, and hydrolysis.

This description includes part or all of the contents as disclosed in the description and/or drawings of Japanese Patent Application No. 2009-157090, which is a priority literature of the present application.

Advantageous Effects of Invention

According to the present invention, it becomes possible to efficiently produce acrolein, which can be used in a wide range of industrial applications, from low-purity glycerin obtained as a by-product during production of biodiesel fuel from waste animal/plant fat or oil using an alkali catalyst.

REFERENCE SIGNS LIST

Figure 1:
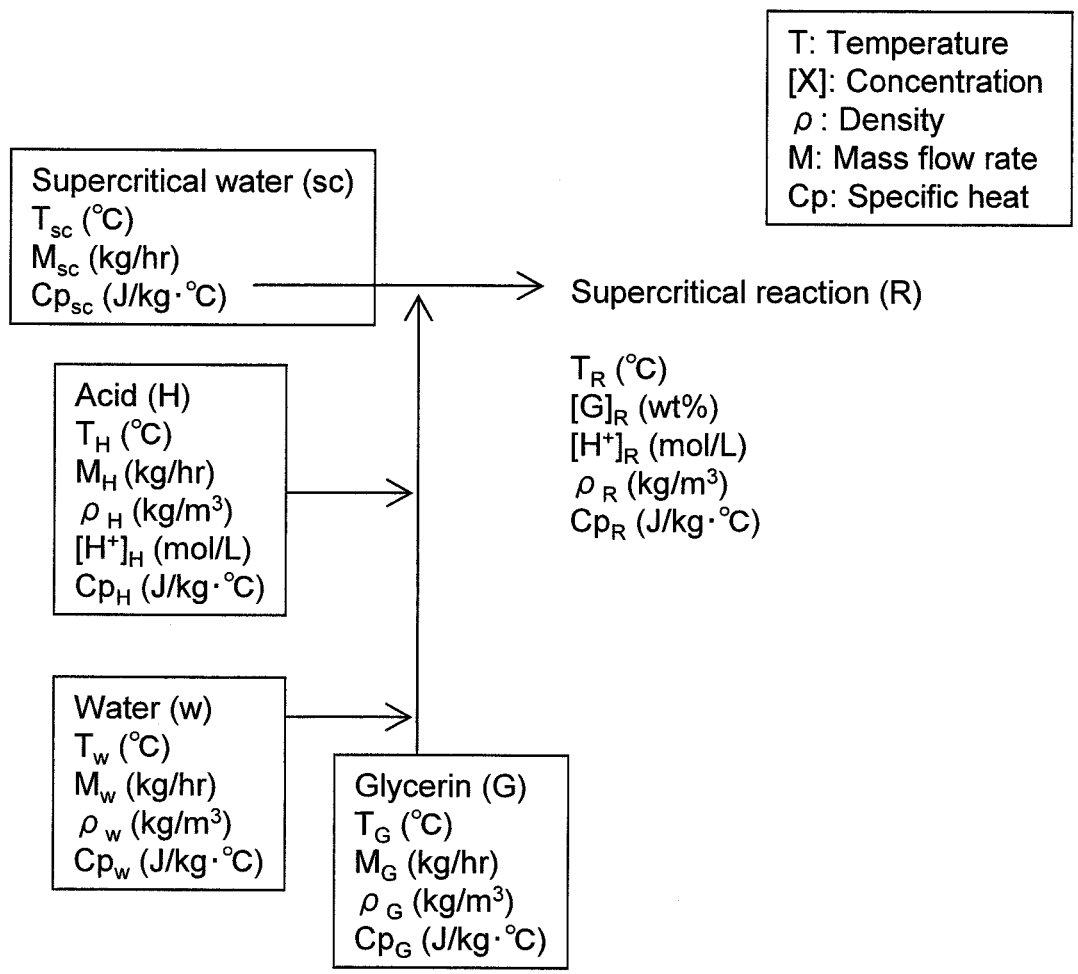
FIG. 1 shows a model diagram for calculating the amount of acid necessary in the supercritical step of the present invention.

15: Acid addition tank
100: pH meter (hydrogen ion concentration determination means)
16: Tank (acid)
101: Agitator
19: Filter (precipitate removal means)
50: Water addition tank
51: Tank (water)
201: Agitator
28: Supercritical reactor (high-temperature and high-pressure reactor)
22: Tank (for supercritical water preparation)
2000: Acrolein production device
3000: Acrolein production device

DESCRIPTION OF EMBODIMENTS

1. Raw Material

In the acrolein production method of the present invention, glycerin separated from a mixture containing glycerin and an ester of monohydric alcohol and fatty acid, wherein the mixture is obtained via transesterification of monohydric alcohol and waste fat or oil containing an ester of fatty acid and glycerin as a main component in the presence of an alkali catalyst, is used as a starting material.

The thus separated glycerin contains water derived from waste fat or oil, water generated via transesterification reaction, an alkali catalyst, and other impurities. The amounts of such components contained in the glycerin are not stable.

It is preferable to carry out a step of obtaining glycerin (i.e., a biodiesel production step) and the method of the present invention together. However, it is also possible to use, as a starting material to be used in the present invention, glycerin obtained as a by-product by separately carrying out a biodiesel production step.

The term "fat or oil" refers to an ester compound comprising higher fatty acid and glycerin, which is mainly composed of triglyceride. Examples of higher fatty acid include lauric acid, myristic acid, palmitic acid, stearic acid, oleic acid, linoleic acid, and linolenic acid.

Fat or oil used herein may be plant fat or oil, animal fat or oil, or a mixture thereof. Here, examples of animal fat or oil include beef tallow, lard, whale oil, and fish oil. Examples of plant fat or oil include soybean oil, rapeseed oil, sesame oil, olive oil, corn oil, palm oil, and peanut oil.

In one aspect, the present invention is characterized in that glycerin obtained as a by-product from waste fat or oil during biodiesel production is used as a starting material. The term "waste fat or oil" refers to waste fat or oil used for cooking and other purposes and then disposed in the food industry including the food service industry, the food production/processing industry, and the like or in general households. In general, waste fat or oil would probably contain impurities such as water, lipid hydroperoxide, free fatty acid, solid foreign substances such as deep-fried tenpura batter (age-kasu), trace metals, and proteins depending on the process of using fat or oil.

Examples of monohydric alcohol used for transesterification reaction with waste fat or oil include methanol, ethanol, 1-propanol, 2-propanol, 1-butanol, and 2-butanol. Of these, methanol is preferable.

According to the present invention, an alkali catalyst is not particularly limited as long as an aqueous solution thereof can be used as a catalyst comprising a substance having an alkaline pH value (pH: more than 7.0). Examples thereof include: an alkali metal hydroxide or oxide such as sodium oxide, potassium oxide, sodium hydroxide, or potassium hydroxide; and an alkaline-earth metal oxide or hydroxide such as calcium oxide. In consideration of availability, reactivity, and the filtration step following the neutralization step, potassium hydroxide or sodium hydroxide is preferable. An alkali catalyst can be used in the form of being supported by an appropriate carrier such as zeolite.

As described above, in one embodiment, the method of the present invention may comprise a transesterification step of carrying out the transesterification of fat or oil with monohydric alcohol by mixing waste fat or oil, an alkali catalyst, and a monohydric alcohol. Mixing and the transesterification step may be carried out simultaneously or alternately. Preferably, mixing and transesterification are simultaneously carried out. As a mixing means, a means for mixing inside pipes such as a line mixer or a static mixer is available. However, in such case, it is difficult to control mixing time. Therefore, it is preferable to carry out continuous or batch introduction of a raw material, an alkali catalyst, and a monohydric alcohol into an agitation tank and then carry out agitation using an agitation means. The agitation means used herein is formed with, for example, a rotational shaft provided with a single or at least two circular, rectangular, triangular, square, or multi-leaf-shaped impellers. The agitation means may be a uniaxial, biaxial, or multiaxial agitation means. According to the present invention, a uniaxial agitation means is preferable. In this step, a mixture comprising glycerin and an ester compound of monohydric alcohol and fatty acid is formed. Glycerin is separated from the ester compound in the glycerin separation step. The glycerin separation step may be carried out by any method involving stationary separation such as separation using a decanter or the like or forced separation such as centrifugation. However, if the amount of the product to be treated is large, forced separation is preferable in terms of cost. Biodiesel (comprising an ester compound as a main component) and glycerin are separated into the light phase and the heavy phase, respectively, in the glycerin separation step. The biodiesel is further subjected to purification treatment such as distillation treatment and thus a biodiesel product is obtained. The thus separated glycerin can be used as a starting material in the acrolein production method of the present invention.

2. Determination Step

The determination step in the present invention is a step of determining the hydrogen ion concentration in glycerin contained in the starting material (comprising water, an alkali catalyst, and other impurities).

The determination step is carried out for the reason described below.

As described in Non-Patent Document 2, the present inventors found that it is desirable that the relation between the glycerin concentration ($[G]_R$) and the hydrogen ion concentration ($[H^+]_R$) in a reaction mixture subjected to a supercritical reaction (i.e., a reaction mixture at the start of the supercritical reaction) expressed by the following equation be satisfied for (at ordinary temperature and pressure conditions, and typically, at 25° C. at 1 atmosphere (and the same applies hereinafter)): $[H^+]_R^2/[G]_R=15$ to 25 mM$^2$/wt % (and particularly desirably 18 to 22 mM$^2$/wt %). In addition, Non-Patent Document 2 describes that the hydrogen ion concentration ($[H^+]_R$) (at ordinary temperature and pressure conditions) of a reaction mixture subjected to a supercritical reaction is preferably 0.1 to 500 mM. It is particularly preferably 5 to 18 mM if the glycerin concentration is 1.5 to 15 wt %. If the hydrogen ion concentration is more than 500 mM, the reaction rate is excessively increased, making it impossible to control the reaction. This causes an increase in production of by-products such as tar and carbon as a result of a minor reaction, making it difficult to design a production apparatus. On the other hand, if the hydrogen ion concentration is less than 0.1 mM, the reactivity decreases, which causes an increase in operation cost due to an increase in reaction time. The hydrogen ion concentration in a reaction mixture subjected to a supercritical reaction is particularly preferably 1 to 100 mM. Further, it is known that the glycerin concentration ($[G]_R$) in a reaction mixture subjected to supercritical reaction is preferably 15 wt % to 30 wt %. This is because if the glycerin concentration is less than 15 wt %, energy efficiency is reduced, causing an increase in operation cost. This is unfavorable in terms of production value. On the other hand, if it is more than 30 wt %, a necessary amount of coordinated water that acts on glycerin cannot be secured. In this case, the minor reaction increasingly influences production, causing a decrease in the yield over the raw material. As described above, it is necessary for supercritical reaction conditions to comply with a variety of requirements.

Therefore, according to the present invention, the hydrogen ion concentration in glycerin contained in a starting material is determined. Based on the determination results, the amount of an acid that should be added in the acid addition step described below and the amount of water that should be contained in a reaction mixture for a supercritical reaction are calculated so as to satisfy the above requirements.

An example of a method for determining the hydrogen ion concentration is a method using a pH meter comprising a quinhydrone electrode, an antimony electrode, a glass electrode, a hydrogen electrode, or the like for determining a pH value based on potential difference. In view of precision, a method for determining a pH value using a glass electrode is preferable. In addition to the method using a pH meter, the hydrogen ion concentration may be determined by titration according to a colorimetric method using an indicator. An indicator preferably used for titration is congo red, methyl orange, bromcresol green, methyl red, bromcresol purple, or the like if glycerin is alcaline.

Alternatively, a small amount of glycerin used as a raw material is sampled and diluted with water. Then, the hydrogen ion concentration in the diluted solution is determined. Accordingly, the hydrogen ion concentration in glycerin used as a raw material can be calculated based on the hydrogen ion concentration in the diluted solution.

3. Acid Addition Step

The acid addition step is a step of adding to glycerin used as a raw material an acid at an amount that is calculated based on the results obtained in the determination step in order to make the glycerin used as a raw material acidic. According to the present invention, "acidity" is defined as corresponding to a pH value of less than 7.0 at ordinary temperature and pressure conditions. The degree of the hydrogen ion concentration for the acidic condition can be adequately determined in a manner such that the hydrogen ion concentration in a mixture eventually subjected to a supercritical reaction satisfies the conditions described in detail in "2. Determination step" above. The means used in the transesterification step can be used as a means for adding acid to glycerin used as a raw material. It is preferable to carry out continuous or batch introduction of an acid and glycerin used as a raw material to an agitation tank, followed by agitation using the above agitation means.

An acid is added to neutralize an alkali catalyst and function as a catalyst in the supercritical reaction. Either an organic acid or an inorganic acid can be used as an acid. Examples of an organic acid include methanesulfonic acid, benzenesulfonic acid, and alkyl sulfonic acid. Examples of an inorganic acid include sulfuric acid, phosphoric acid, acetic acid, and nitric acid. However, sulfuric acid having strong dehydration or catalytic action is preferable.

4. Precipitate Removal Step

When glycerin is neutralized in the acid addition step, a salt is formed with an alkali catalyst and an acid. The type of salt is determined based on a combination of an alkali catalyst and an acid. However, typical examples of the salt include sodium sulfate, potassium sulfate, calcium sulfate, and calcium chloride.

In general, the salt is highly soluble in water but poorly soluble in supercritical water due to a decrease in permittivity. Probably, there would be a risk of pipe occlusion or the like if a precipitation phenomenon were to take place in supercritical water.

Therefore, according to the present invention, it is preferable to avoid the above risk in the following manner: the above salt is allowed to precipitate in the form of a hydrated salt or anhydrous salt after neutralization of glycerin in the acid addition step or after the end of the acid addition step, but before the start of the supercritical water treatment step, followed by removal of the salt by a general separation means such as filtration or centrifugation. As a result of removal of the precipitate, operation efficiency can be improved in the supercritical water treatment step. It is possible to separate or remove the precipitate after neutralization of glycerin in the acid addition step and further add an acid to glycerin from which the precipitate has been removed to terminate the acid addition step. Alternatively, it is also possible to separate or remove the precipitate after the end of the acid addition step.

The present inventors found that when the moisture content in glycerin is lower than the stoichiometric quantity of water that allows hydration of the total amount of salt in glycerin, a hydrated salt or anhydrous salt can be precipitated in glycerin. This finding is specifically described below. For instance, salts such as sodium sulfate, potassium sulfate, calcium sulfate, and calcium chloride are known for forming decahydrate, monohydrate, dihydrate, and hexahydrate at 32.4° C. or less, 9.7° C. or less, 42° C. or less, and 37.1° C. or less, respectively. Specifically, regarding "the stoichiometric quantity of water that allows hydration of the total amount of salt," when sodium sulfate, potassium sulfate, calcium sulfate, and calcium chloride are used at an amount of 1 mole each, water is used at amounts of 10 moles, 1 mole, 2 moles, and 6 moles, respectively. This indicates that, in the cases of sodium sulfate, potassium sulfate, calcium sulfate, and calcium chloride, the weights of moisture absorbed as crystal water by a salt are 2.25, 0.16, 0.49, and 1.46 times greater than the weights of an alkali metal or alkaline-earth metal hydroxide to be introduced, respectively. Therefore, if the moisture content in glycerin used as a raw material and an acid to be added falls below the above relevant range for the salt, it is theoretically possible for the total amount of a hydrate of a salt to form a solid precipitate in the mixed solution of glycerin and acid. Thus, by separating and removing the precipitate using a separation means such as filtration or centrifugation, a remaining catalyst such as an alkali metal or an alkaline-earth metal can be removed with high efficiency.

If a precipitate is formed and the precipitate contains an anhydrous salt, it is possible to confirm that the moisture content in glycerin is lower than the stoichiometric quantity of water that allows hydration of the total amount of salt in glycerin. The presence or absence of an anhydrous salt can be checked by a usual means such as an X-ray diffraction pattern.

In general, it is possible to achieve the appropriate moisture content in glycerin to which an acid has been added, without especially carrying out moisture adjustment treatment, by, for example, increasing the acid concentration in an aqueous solution when the acid is added in the form of an aqueous solution. In another embodiment of the present invention, a moisture adjustment step of cooling glycerin and/or removing moisture is carried out in order to reduce the moisture content in glycerin after the acid addition to below the above stoichiometric quantity. Cooling of glycerin causes crystalline phase transition and hydrate formation as described above. Therefore, water in glycerin is absorbed by a hydrated salt, resulting in precipitation. Thus, an excessive amount of the salt is precipitated in the form of an anhydrous salt. Moisture can be removed by moisture adsorption using zeolite or a moisture-absorbing resin, separation using a separation membrane, distillation, or the like. After moisture removal, the moisture concentration in glycerin can be determined using a Karl Fischer moisture titrator or the like.

A precipitate of a salt formed as a result of precipitation can be removed by a usual means such as filtration or centrifugation. The type of filter used for filtration is, for example, a filler made of a material having a porous structure such as ceramics or active carbon, a metal having a mesh structure, a fibrous material having a fiber structure, or the like. It can be adequately determined depending on the particle diameter of the precipitate.

5. Supercritical Water Treatment Step

The supercritical water treatment step is a step of allowing supercritical water to act on glycerin to which an acid has been added in the above acid addition step, and preferably, glycerin from which a precipitate has been further removed so as to prepare acrolein.

In addition, it is preferable to confirm the pH value of glycerin again before allowing supercritical water to act on glycerin to which an acid has been added in the above acid addition step, and preferably, glycerin from which a precipitate has been further removed.

According to the present invention, the term "supercritical water" refers to water at a temperature exceeding the water critical temperature (Tc) and a pressure exceeding the critical pressure of water (Pc). Therefore, in the supercritical water treatment step, a mixture of glycerin and water is treated under high-temperature and high-pressure conditions that allow water contained in the mixture to have a temperature of more than 374° C. and a pressure of 22.06 MPa or more. The water temperature conditions (i.e., the reaction temperature conditions) range preferably from 380° C. to 550° C. and more preferably from 400° C. to 500° C. If the temperature is less than 380° C., a minor reaction tends to proceed, which is problematic. If the temperature is more than 550° C., such high temperature is inappropriate in terms of industrial use. The water pressure conditions (i.e., reaction pressure conditions) range preferably from 25 to 50 MPa and more preferably from 30 to 45 MPa. If the pressure is less than 25 MPa, the proton concentration in a reaction mixture decreases, making it difficult for a reaction to proceed. This is problematic. If the pressure is more than 50 MPa, there are few advantages of high pressurization. Further, the cost of securing the structural strength of a filter apparatus or the like for removal of by-products increases. Such high pressure is inappropriate for industrial use, which is problematic.

As described in "2. Determination step" above, optimal solutions for the reaction time and the acid concentration (hydrogen ion concentration) in the supercritical water treatment step depend on the concentration of glycerin used as a raw material. The optimal acid concentration is proportional to the square root of the glycerin concentration. In addition, the optimal reaction time is inversely proportional to the glycerin concentration. Therefore, the reaction time is preferably 0.1 to 100 seconds and more preferably 0.5 to 10 seconds.

An example of a reactor used in the supercritical water treatment step is a tube-type or tank-type reactor. However, in view of shortening the reaction time, a tube-type reactor is preferable. Glycerin mixed with supercritical water is heated to the reaction temperature while passing through a tube by an external heating means such as a heater or a heating medium. Accordingly, a dehydration reaction is induced such that acrolein is produced.

6. Water Addition Step

Figure 2:
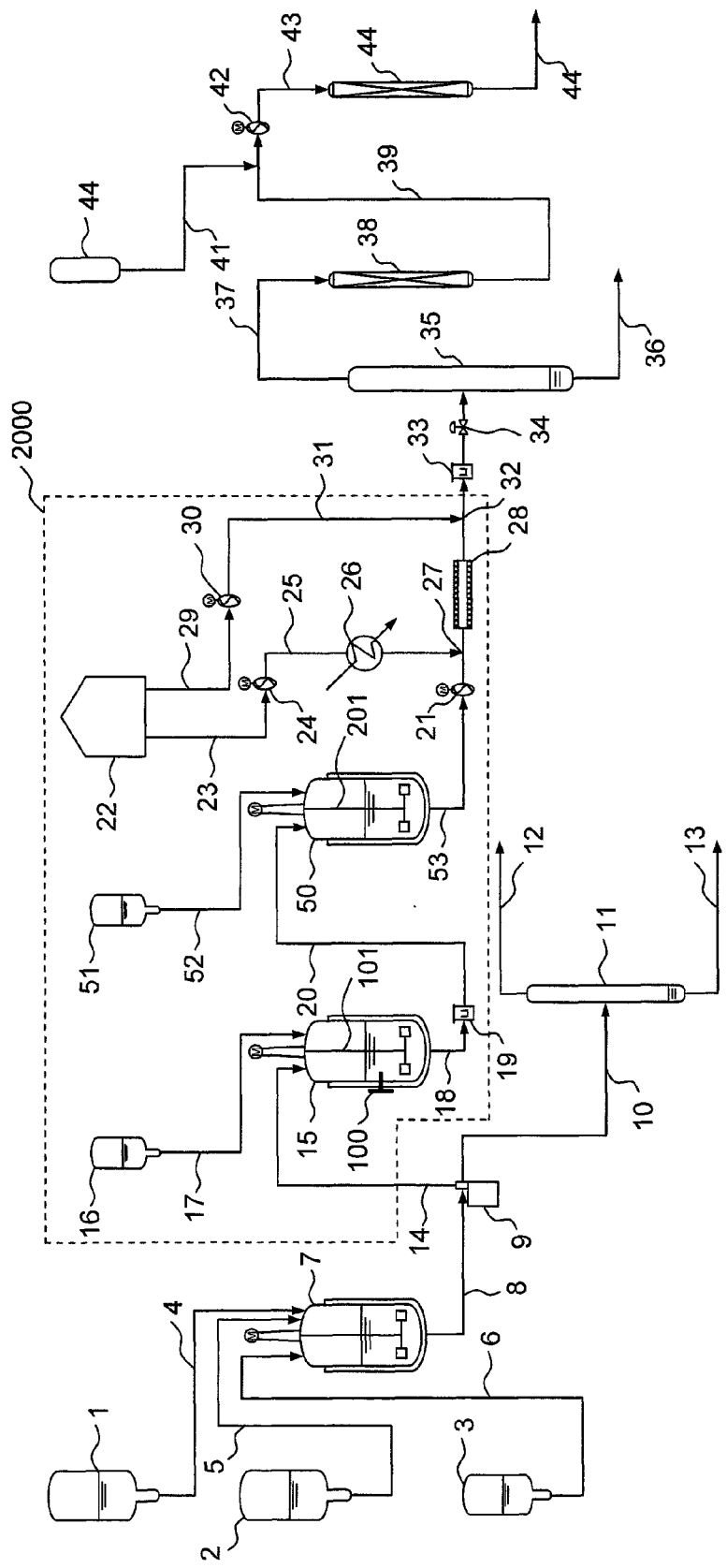
FIG. 2 schematically shows an apparatus for carrying out all steps of the present invention used in one embodiment.
Figure 3:
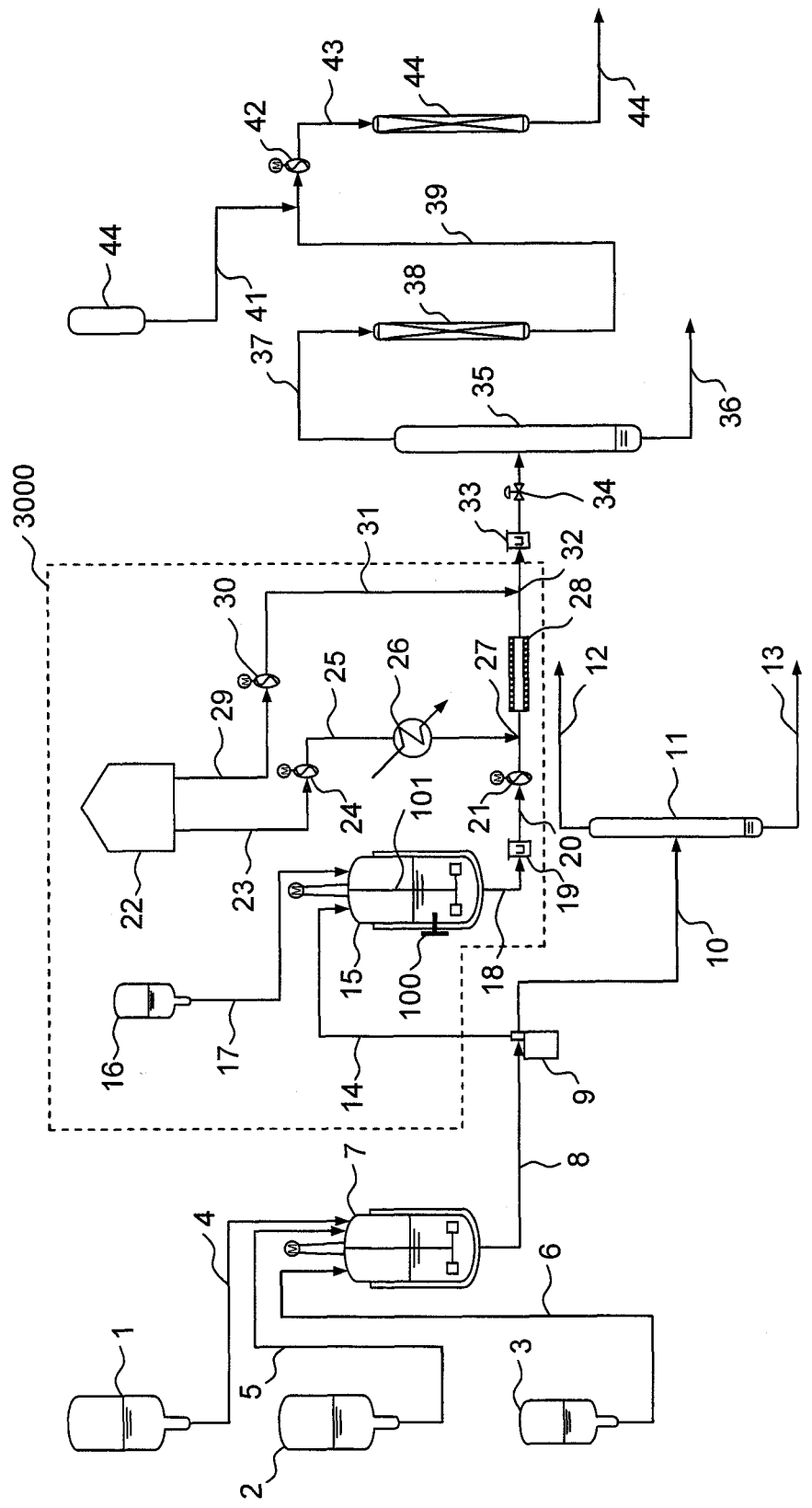
FIG. 3 schematically shows an apparatus for carrying out all steps of the present invention used in another embodiment.

The moisture concentration in a reaction mixture at the start of the supercritical reaction is determined such that various requirements described in "2. Determination step" above are satisfied. As shown in FIG. 3 described below, it is possible to control the moisture concentration in the reaction mixture by controlling the flow rate of water (water from a pipe 25) (hereinafter referred to as "supercritical water") at a temperature or pressure similar to critical conditions for water. Such water is mixed with glycerin after the acid addition step (preferably after the precipitate removal step). However, as shown in FIG. 2, a means for adding water to glycerin after the acid addition step (preferably after the precipitate removal step) (numerals 50 to 53 in FIG. 2) is arranged downstream of the precipitate removal means and upstream of the supercritical water treatment means, in addition to the flow path in which supercritical water (water from a pipe 25) joins the main flow. Thus, it becomes possible to finely adjust the amount of water added while maintaining the flow rate of supercritical water (water from a pipe 25) at a stable rate. Thus, an industrially applicable method is provided.

In addition, the present inventors found that when the mass flow rate of supercritical water is designated as $M_{sc}$, the mass flow rate $M_w$ of water (including water derived from neutralization with acid) used for fine adjustment and the amount of acid added $M_H$ can be calculated based on the pH value of glycerin used as a raw material determined in the determination step.

FIG. 1 shows a model chart for a method for calculating the concentration of acid that should be added to glycerin based on the determined pH.

FIG. 1 shows a model chart in which an acid and water are added to glycerin having a predetermined pH used as a raw material and the glycerin is reacted with supercritical water. In FIG. 1, T denotes fluid temperature, [H$^+$] denotes the hydrogen ion concentration, [G] denotes the glycerin concentration, p denotes the density, M denotes the mass flow rate, and Cp denotes specific heat. In addition, indexes shown lower right of symbols (sc, H, w, G, and R) denote the relevant lines.

The following approximation is possible for the supercritical reaction of the present invention in practice:

$$T_H = T_w = T_G, \; Cp_{sc} = Cp_H = Cp_w = Cp_G = Cp_R. \quad \text{[Equation 1]}$$

The following equations are valid with respect to (1) glycerin mass balance, (2) [H$^+$] mass balance, and (3) enthalpy balance.

$$M_G = (M_{sc} + M_H + M_W + M_G) \cdot [G]_R \quad \text{[Equation 2]}$$

$$\frac{10^3 \times [H^+]_H}{\rho_H} \times M_H - \frac{10^3 \times 10^{pH-14}}{\rho_G} \times M_G \approx \\ \frac{10^3 \times [H^+]_R}{\rho_R} \times (M_{sc} + M_H + M_W + M_G) \quad \text{[Equation 3]}$$

$$Cp_{sc} M_{sc} T_{sc} + Cp_H M_H T_H + Cp_w M_w T_w + Cp_G M_G T_G = \\ Cp_R (M_{sc} + M_H + M_W + M_G) \cdot T_R \quad \text{[Equation 4]}$$

$$(M_H + M_w + M_G) = M_{sc} \frac{(T_R - T_{sc})}{(T_H - T_R)} \quad \text{[Equation 5]}$$

When Equation 5 is substituted into Equation 2, the following is valid.

$$M_G = \left[ M_{sc} \frac{(T_H - T_{sc})}{(T_H - T_R)} \right] \cdot [G]_R \quad \text{[Equation 6]}$$

When Equation 2 and Equation 6 are substituted into Equation 3, the following is valid.

$$M_H = \frac{\rho_H}{[H^+]_H} \times M_{sc} \times \frac{(T_H - T_{sc})}{(T_H - T_R)} \left\{ \frac{[H^+]_R}{\rho_R} + \frac{10^{pH-14}}{\rho_G} \cdot [G]_R \right\} \quad \text{[Equation 7]}$$

When Equation 6 and Equation 7 are substituted into Equation 5, the following is valid.

$$M_W = M_{sc} \cdot \frac{(T_H - T_{sc})}{(T_H - T_R)} \left[ 1 - [G]_R - \frac{(T_H - T_R)}{(T_H - T_{sc})} + \frac{\rho_H}{[H^+]_H} \times \left\{ \frac{[H^+]_R}{\rho_R} + \frac{10^{pH-14}}{\rho_G} \cdot [G]_R \right\} \right] \quad \text{[Equation 8]}$$

Based on the above, the necessary amounts of acid and water added $M_H$ and $M_w$ can be determined based on the determined pH for glycerin.

Specifically, the method of the present invention comprises a step of adding water used in the supercritical water treatment step at a pressure below the critical pressure of water to glycerin after the acid addition step or the precipitate removal step if the precipitate removal step is carried out. The method also comprises a step of adding water used in the supercritical water treatment step at a pressure above the critical pressure of water to such glycerin. Here, "water at a pressure below the critical pressure of water" is generally added by a means other than a high pressure pump or the like. Such water is usually added at a pressure of 0.1 MPa to 3.0 MPa and a temperature of 5° C. to 40° C. In general, "water at a pressure above the critical pressure of water" is pressurized for addition by a high pressure pump or the like. Here, the pressure is preferably 30 MPa to 45 MPa and the temperature is preferably 400° C. to 550° C. upon addition. Conditions comprising the mass flow rate $M_{sc}$ of "water at a pressure above the critical pressure of water," the desired acid concentration, and the desired glycerin concentration are determined. Then, the mass flow rate $M_t$ of "water at a pressure below the critical pressure of water" can be determined by Equation 8 based on the hydrogen ion concentration in glycerin determined in the determination step.

7. Other Steps

The method of the present invention can comprise a step of cooling acrolein prepared by a supercritical reaction. Cooling is carried out to terminate the supercritical reaction. In view of reaction control, it is necessary for the cooling time to become remarkably shorter than the reaction time. Therefore, the cooling time is preferably 0.01 to 10 seconds and more preferably 0.05 to 1 second. A heat exchanger may be used as a cooling means. However, in view of the relation to the cooling time described above, direct contact via mixing with a cooling medium is preferable. In addition, in order to prevent contamination due to mixing, it is preferable to use water.

The method of the present invention comprises a step of removing solid matter prepared from cooled acrolein in a minor reaction of the supercritical reaction. As a removal method, a sedimentation separation system such as a decanter or the like can be used. However, for shortening the treatment time, simple filtration using a filter is preferable. The type of filter used for filtration is, for example, a filler made of a material having a porous structure such as ceramics or active carbon, a metal having a mesh structure, a fibrous material having a fiber structure, or the like. It can be adequately determined depending on the precipitate particle diameter.

The method of the present invention can further comprise a step of purifying filtrated acrolein. Crude acrolein contains unreacted glycerin, acid, tar or allyl alcohol generated by a minor reaction, and the like. All of them are high-boiling-point components of acrolein. Therefore, separation by distillation is desirable.

The method of the present invention can further comprise a step of hydrating purified acrolein. In the hydration step, acrolein containing water is allowed to pass through a column filled with a cation-exchange resin. The reaction temperature is 30° C. to 150° C. and preferably 40° C. to 100° C. 3-hydroxypropanal can be obtained by hydrating acrolein.

The method of the present invention can further comprise a step of hydrogenating 3-hydroxypropanal obtained via hydration. In this step, a raw material is hydrogenated, followed by reaction in the presence of a catalyst. The reaction temperature is 40° C. to 200° C. and preferably 70° C. to 180° C. The reaction pressure is 0.5 to 20 MPa and preferably 5 to 15 MPa. In addition, examples of a catalyst used in the hydrogenation step include metals such as nickel, platinum, and tungsten. In order to increase the yield, platinum is preferably used. As a result of hydrogenation of hydroxypropanal, 1,3-propanediol can be obtained. A 1,3-propanediol product can be obtained by purifying and separating unreacted acrolein, unreacted hydroxypropanal, and the like from the obtained crude 1,3-propanediol.

One embodiment of an apparatus for carrying out the method of the present invention is shown in FIG. 2. However, the apparatus of the present invention is not limited thereto.

The 1,3-propanediol production process shown in FIG. 2 comprises the following 10 steps: a fat or oil (raw material) mixing/BDF (biodiesel fuel) preparation step; a BDF separation step; a pH measurement/acid addition step; a precipitate separation step; a water addition step; a supercritical water treatment step; a solid matter separation step; an acrolein purification step; a hydration step; and a hydrogenation step.

In the fat or oil (raw material) mixing/BDF preparation step, fat or oil used as a raw material, an alkali catalyst, and monohydric alcohol are supplied to a BDF preparation tank 7 from tanks 1, 2, and 3 via pipes 4, 5, and 6, respectively. A transfer system such as a pump is provided to the pipes 4, 5, and 6 according to need. BDF preparation proceeds during mixing in the tank 7. The reactant is transferred through a pipe 8 and goes on to the separation step. A forced separation apparatus 9 such as a centrifuge is provided for the separation step for continuous separation of supplied crude BDF into light BDF and a heavy glycerin aqueous solution. The thus separated BDF is transferred through a pipe 10 so as to be purified in a purification tower 11. Thus, a BDF product is obtained from a pipe 12.

Meanwhile, the separated glycerin aqueous solution is transferred through a pipe 14 to an acid addition tank 15. The pH of the glycerin aqueous solution is measured in the tank 15. pH measurement can be carried out by a usual means. A pH meter 100 is shown in FIGS. 2 and 3. However, a pH meter used in the present invention is not limited thereto. A small amount of a glycerin aqueous solution is sampled from a tank 15 and diluted with water. The pH concentration of the dilute solution is determined. The pH value of the glycerin aqueous solution in the tank 15 can be calculated based on the pH value of the diluted solution. Based on the pH value of the glycerin aqueous solution in the tank 15, the acid concentration and the amount of water to be added are calculated in order to achieve a desired hydrogen ion concentration and a desired glycerin concentration in a reaction mixture that is subjected to a supercritical reaction in the subsequent step. The acid in the tank 16 is transferred through a pipe 17 to the tank 15 and mixed by an agitator 101 provided to the tank 15. When pH inside the tank 15 reaches an appropriate level, transfer of the acid from the tank 16 is terminated.

The glycerin aqueous solution subjected to pH adjustment is transferred through a pipe 18 to a filter 19. Precipitates generated due to acid addition and the like are removed using the filter 19.

Subsequently, the glycerin aqueous solution is transferred through a pipe 20 to a water addition tank 50. Water at an amount calculated based on the pH value in the tank 15 is transferred through a pipe 52 to the tank 50 from a tank 51 so as to be mixed by an agitator 201 provided to the tank 50. When the predetermined amount of water has been supplied to the tank 50, transfer of water from the tank 51 is terminated.

The glycerin aqueous solution after the water addition is supplied through a pipe 53 to a high pressure pump 21. The glycerin aqueous solution is pressurized by the pump 21 to the critical pressure of water and then mixed with water supplied from the tank 22 in a pipe 28. Water from the tank 22 is transferred through a pipe 23 and pressurized by a high pressure pump 24. For preheating water, a heat exchanger 26 is provided to a pipe 25 such that water is heated close to the critical temperature of water.

The mixture of the glycerin aqueous solution and water is transferred to a supercritical reactor 28. An electric heater is provided to the reactor 28 for heating to the reaction temperature.

According to the present invention, a supercritical water treatment means (or a high-temperature and high-pressure water treatment means) is provided with a supercritical water preparation means composed of a tank 22, a pipe 23, a high pressure pump 24, a heat exchanger 26, and a pipe 25; a high pressure pump 21; and a supercritical reactor 28. It is configured such that supercritical water (or high-temperature and high-pressure water) is transferred through a pipe 25 provided to the supercritical water preparation means so that water joins the flow in a pipe unit 27 connecting the high pressure pump 21 and the supercritical reactor 28.

A mixture containing acrolein prepared in the supercritical reaction is discharged from a pipe 32. The mixture is mixed with cooling water supplied from the tank 22 in the pipe 32. Cooling water is pressurized by a high pressure pump 30 and mixed with high-pressure fluid in the pipe 32.

Cooling of the mixture causes precipitation of solid matter. The solid matter is removed by a filter 33. Then, the mixture is depressurized by a pressure reducing valve 34 and transferred to a purification tower 35 to purify acrolein. At such time, high-boiling-point components such as glycerin and acid are removed from the tower bottom and discharged through a pipe 36. Accordingly, acrolein, which is a low-boiling-point component, can be obtained from the tower top. Purified acrolein is transferred through a pipe 37 to a hydration reactor 38. The reactor 38 is made of an ion-exchange resin and provided with a heating apparatus. The hydration reaction proceeds as a result of introduction of acrolein into the reactor 38.

Propionaldehyde prepared by hydration is transferred through a pipe 39 and goes on to the hydrogenation step. A tank 40 is filled with hydrogen such that hydrogen is mixed with propionaldehyde in a pipe 39 via a pipe 41. The hydrogenation reaction is carried out under high pressure. Therefore, the pipe is provided with a high pressure pump 42 to pressurize to the reaction pressure so as to supply the mixture through a pipe 43 to a hydrogenation reactor 44.

The reactor 44 is composed of a column filled with a catalyst and a heating apparatus. As a result of reaction in the reactor 44, 1,3-propanediol can be obtained.

The apparatus shown in FIG. 2 can the addition amount of water by adequately adjusting the amount of water added to the tank 50, while maintaining the predetermined amount of water supplied ($M_{sc}$) at a pressure above the critical pressure of water supplied from the tank 22 through the pipe 23, the high pressure pump 24, and the pipe 25. Therefore, the apparatus is advantageous in terms of ease of use in practice of industrial production.

Further, FIG. 3 shows an apparatus for carrying out the method of the present invention in another embodiment. In the embodiment shown in FIG. 3, the apparatus has a configuration similar to that of the apparatus shown in FIG. 2 except that it does not include a water addition tank 50, a tank 51, and pipes 52 and 53. In the embodiment shown in FIG. 3, the amount of water supplied at a pressure above the critical pressure of water from the tank 22 via the pipe 23, the high pressure pump 24, and the pipe 25 is adjusted. This makes it possible to ensure the amount of water to be added which is calculated based on the pH value of the glycerin aqueous solution in the tank 15 in order to achieve a desired hydrogen ion concentration and a desired glycerin concentration in a reaction mixture that is subjected to a supercritical reaction. Functions and structures of the other component members of the apparatus shown in FIG. 3 are identical to the functions and structures of component members with the identical numerals elaborated based on FIG. 2. Therefore, explanation of the members is omitted for FIG. 3.

The present invention is hereafter described in greater detail with reference to the following examples, although the scope of the present invention is not limited thereto.

EXAMPLES

Example 1

BDF Production

Soybean oil was selected as a raw material oil for BDF. The fatty acid composition excluding the glycerin component was as follows: palmitic acid: 8 wt %; stearic acid: 5 wt %; oleic acid: 27 wt %; linoleic acid: 53 wt %; and linolenic acid: 7 wt %.

First, methanol (2 L) was added to sodium hydroxide (35 g), followed by mixing for 20 minutes. The raw material soybean oil (10 L) was heated to 55° C. and the mixed methanol solution was gently added thereto. The mixture was agitated for approximately 1 hour at a maintained temperature. Then, the mixture was cooled and allowed to stand still for 20 hours. Biodiesel fuel (approximately 10 liters) separated in the upper phase was siphoned. The glycerin solution (2 L) was left in the lower phase.

<pH Adjustment>

Two drops of a pH indicator (methyl red) was added to the glycerin solution, followed by agitation. The solution turned yellow. Concentrated sulfuric acid (concentration: 90 wt % (and the same applies hereinafter)) was added dropwise (at one drop each) to the solution during agitation. When the solution turned red, the addition of concentrated sulfuric acid was suspended. At such time, the pH value of the glycerin solution was 7.

In this experiment, it was intended to achieve a desired glycerin concentration ($[G]_R$) of 15 wt % and a desired hydrogen ion concentration ($[H^+]_R$) of 18 mM of the reaction mixture at the start of the supercritical reaction. In such case, the following is valid: $[H^+]_R^2/[G]_R = 18^2/15 = 21.6$ mM$^2$/wt %.

In order to achieve the above desired hydrogen ion concentration after the water addition step, concentrated sulfuric acid (16 g) was further added to the glycerin solution (pH=7), followed by agitation. Alternatively, this additional concentrated sulfuric acid may be added in the latter stage of the next precipitate removal step.

<Precipitate Removal>

In an environment at a room temperature of 20° C., a mixture of sodium sulfate decahydrate and anhydride resulted in deposition of a colorless and transparent slurry precipitate in a mixed solution of glycerin/sulfuric acid as a result of neutralization. The resultant was filtered to remove sodium. The weight of the separated precipitate was found to be 130 g. The precipitate was introduced into an X-ray diffraction apparatus so as to confirm that the precipitate had been obtained as a mixture of sodium sulfate decahydrate and anhydride. In addition, the acid concentration in the solution was found to be approximately 0.15 M, which corresponds to the concentration of diluted sulfuric acid. Here, it is desirable to use a filter for filtration that is made of an acid-tolerant alloy, fabric, or paper unsusceptible to corrosion or the like.

<Water Addition>

A glycerin aqueous solution was prepared by adding distilled water (14.3 L) to the mixture solution of glycerin/sulfuric acid from which the precipitate had been removed so as to result in a glycerin concentration of 15 wt % and a hydrogen ion concentration of 18 mM.

<Supercritical Reaction>

The 15 wt % glycerin aqueous solution at a hydrogen ion concentration of 18 mM was pressurized with a high pressure pump to 35 MPa and the flow rate was stabilized at 250° C. When the pressure became stable, a heater provided to the reactor was controlled so as to immediately adjust the liquid temperature inside the reactor to 400° C. The aqueous solution was introduced into the controlled reactor to carry out a reaction for 2 seconds.

<Cooling>

Distilled water at 20° C. was added into the pipe at a flow rate of 6 mL/s in order to immediately cool the introduced aqueous solution to 200° C.

<Precipitate Removal/Cooling/Depressurization>

Accordingly, a carbon precipitate was formed in the solution and removed with a filter. Further, the precipitate was cooled. The pressure was returned to ordinary pressure using a pressure reducing valve. As a result, glycerin was successfully converted into acrolein at a yield of 70%.

<Distillation>

A batch-type simple distillation apparatus was used to remove high-boiling-point components such as sulfuric acid, unreacted glycerin, and tar from the solution for purification of acrolein. As a result, an acrolein solution (1.4 L) was obtained.

<Hydration>

The moisture concentration of the acrolein solution was determined using a Karl Fischer moisture titrator to calculate the moisture content required in the hydration step. Water (5.1 L) was added to the acrolein solution so as to adjust the acrolein concentration to 20 wt %. Then, the acrolein aqueous solution was allowed to pass through a column filled with an ion-exchange resin at a flow rate of 0.35 mL/s. The solution was heated by a heater to adjust the outlet liquid temperature to 50° C. As a result, acrolein was successfully converted to 3-hydroxypropionaldehyde at a conversion rate of 76%.

<Hydrogenation>

The 3-hydroxypropionaldehyde aqueous solution obtained by hydration was pressurized to 15 MPa using a high pressure pump and then the flow rate was stabilized. Hydrogen was added at the middle of the pipe at a flow rate of 7.5 NmL/s from the hydrogen cylinder. The mixture was allowed to pass through a column filled with platinum and nickel at a flow rate of 1.7 mL/s. The column was provided with a heater and the outlet temperature was set to 60° C. As a result, 3-hydroxypropionaldehyde was successfully converted to 1,3-propanediol (1,3-PDO) at a conversion rate of 99%. Thus, 1,3-PDO was successfully synthesized from glycerin used as a raw material at a yield of 53%.

Example 2

Glycerin Concentration

In this experiment, it was intended to achieve a desired glycerin concentration ($[G]_R$) of 50 wt % and a desired hydrogen ion concentration ($[H^+]_R$) of 18 mM of the reaction mixture at the start of the supercritical reaction. At such glycerin concentration and hydrogen ion concentration, the following is valid: $[H^+]_R^2/[G]_R = 18^2/50 = 6.48$ mM$^2$/wt %.

A reaction was carried out under conditions similar to the conditions used in Example 1 except that concentrated sulfuric acid (4 g) was added to adjust the hydrogen ion concentration to 18 mM upon <pH adjustment> and water (2.5 L) was added to adjust the glycerin concentration to 50 wt % upon <Water addition> in Example 1.

As a result, the acrolein yield was found to be 10%. In addition, tar and carbon particles were confirmed to be present at large amounts in the reacted solution.

Example 3

Hydrogen Ion Concentration

In this experiment, it was intended to achieve a desired glycerin concentration ($[G]_R$) of 15 wt % and a desired hydrogen ion concentration ($[H^+]_R$) of 6 mM of the reaction mixture at the start of the supercritical reaction. At such glycerin concentration and hydrogen ion concentration, the following is valid: $[H^+]_R^2/[G]_R = 6^2/15 = 2.4$ mM$^2$/wt %.

Figure 4:
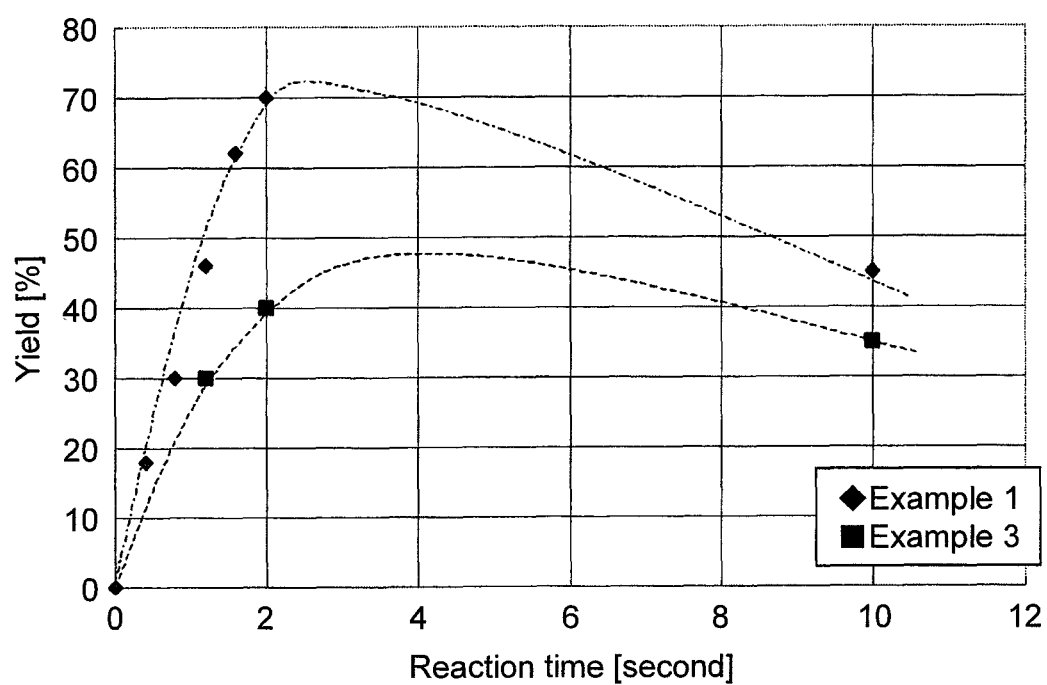
FIG. 4 is a graph showing results of an acrolein yield comparison of Example 1 and Example 3.

A reaction was carried out under conditions similar to the conditions used in Example 1 except that sulfuric acid (9.7 g) was added after titration upon <pH adjustment> in Example 1. The hydrogen ion concentration in the aqueous solution obtained by adding water to the mixed solution (glycerin/sulfuric acid) was found to be 6 mM corresponding to one-third (⅓) that in Example 1. As a result, the acrolein yield was found to be 40%. FIG. 4 shows a comparison of Example 3 with Example 1.

INDUSTRIAL APPLICABILITY

According to the method for producing acrolein from waste fat or oil of the present invention, the cost of a raw material for an acrolein product can be reduced with the use of glycerin removed from biodiesel as a raw material for a high-value-added product without highly purifying such glycerin. Therefore, the present invention is highly industrially applicable.

All publications, patents, and patent applications cited herein are incorporated herein by reference in their entirety.

The invention claimed is:

1. A method for producing acrolein, wherein acrolein is produced by allowing supercritical water to act on glycerin separated from a mixture containing glycerin and an ester of monohydric alcohol and fatty acid, wherein the mixture is obtained via transesterification of monohydric alcohol and waste fat or oil containing as a main component an ester of fatty acid and glycerin in the presence of an alkali catalyst, the method comprising:

a determination step of determining the hydrogen ion concentration in glycerin;

an acid addition step of adding to the glycerin an acid at an amount calculated based on the results of the determination step so as to make the glycerin acidic;

a moisture adjustment step of cooling glycerin and/or removing moisture so as to achieve the moisture content in after the acid addition step to be lower than the stoichiometric quantity of water that allows hydration of the total amount of the salt in the glycerin;

a supercritical water treatment step of allowing supercritical water to act on the glycerin after the acid addition so as to produce acrolein from the glycerin; and a precipitate removal step of causing a precipitate of a salt formed from the alkali catalyst and the acid in the glycerin after glycerin neutralization in the acid addition step or after the end of the step and before the start of the supercritical water treatment step so as to separate and remove the precipitate, wherein the alkali catalyst is an oxide or hydroxide of an alkali metal or alkaline-earth metal, and the acid is an inorganic acid.

2. The method according to claim 1, which further comprises: a step of adding water used in the supercritical water treatment step at a pressure below the critical pressure of water to glycerin after the precipitate removal step; and a step of adding water used in the supercritical water treatment step at a pressure above the critical pressure of water to the glycerin.

3. A method for producing acrolein, wherein acrolein is produced by allowing high-temperature and high-pressure water to act on glycerin separated from a mixture containing glycerin and an ester of monohydric alcohol and fatty acid, wherein the mixture is obtained via transesterification of monohydric alcohol and waste fat or oil containing as a main component an ester of fatty acid and glycerin in the presence of an alkali catalyst, the method comprising:

a determination step of determining the hydrogen ion concentration in glycerin;

an acid addition step of adding to the glycerin an acid at an amount calculated based on the results of the determination step so as to make the glycerin acidic;

a moisture adjustment step of cooling glycerin and/or removing moisture so as to achieve the moisture content in after the acid addition step to be lower than the stoichiometric quantity of water that allows hydration of the total amount of the salt in the glycerin;

a high-temperature and high-pressure treatment step of adding water to the glycerin after the acid addition and treating the obtained mixture under high-temperature and high-pressure conditions so as to produce acrolein from the glycerin; and a precipitate removal step of causing a precipitate of a salt formed from the alkali catalyst and the acid in the glycerin after glycerin neutralization in the acid addition step or after the end of the step and before the start of the high-temperature and high-pressure treatment step so as to separate and remove the precipitate, wherein the alkali catalyst is an oxide or hydroxide of an alkali metal or alkaline-earth metal, and the acid is an inorganic acid.

4. The method according to claim 3, wherein the high-temperature and high-pressure treatment step is a step of treating the mixture of the glycerin to which the acid has been added and water by adjusting the water temperature to 374° C. or more and the water pressure to 22.06 MPa or more in the mixture.

5. The method according to claim 3, which further comprises:

a step of adding water used in the high-temperature and high-pressure water treatment step at a pressure below the critical pressure of water to glycerin after the precipitate removal step; and a step of adding water used in the high-temperature and high-pressure water treatment step at a pressure above the critical pressure of water to the glycerin.

6. A device for producing acrolein by allowing supercritical water to act on glycerin, which comprises:

a means for determining the hydrogen ion concentration in glycerin used as a raw material;

an acid addition tank for adding an acid to the glycerin used as a raw material provided with a means for supplying the glycerin, a means for supplying the acid, and an agitation means;

a moisture adjustment means for cooling glycerin and/or removing moisture so as to achieve the moisture content in after the acid addition tank to be lower than the stoichiometric quantity of water that allows hydration of the total amount of the salt in the glycerin;

a supercritical water treatment means for allowing supercritical water to act on glycerin supplied from the acid addition tank, which is located downstream of the acid addition tank; and a precipitate removal means for separating and removing a precipitate in glycerin supplied from the acid addition tank and supplying the glycerin from which the precipitate has been removed to the supercritical water treatment means, the precipitate removal means being arranged downstream of the acid addition tank and upstream of the supercritical water treatment means, wherein the acid is an inorganic acid.

7. The device according to claim 6, which further comprises a water addition tank for adding water to glycerin from which the precipitate has been removed provided with a means for supplying the glycerin from the precipitate removal means, a means for supplying water, and an agitation means, the tank being arranged downstream of the precipitate removal means and upstream of the supercritical water treatment means, and wherein glycerin to which water has been added in the water addition tank is supplied to the supercritical water treatment means.

8. A device for producing acrolein by allowing high-temperature and high-pressure water to act on glycerin, which comprises:

a means for determining the hydrogen ion concentration in glycerin used as a raw material;

an acid addition tank for adding an acid to the glycerin used as a raw material provided with a means for supplying the glycerin, a means for supplying the acid, and an agitation means;

a moisture adjustment means for cooling glycerin and/or removing moisture so as to achieve the moisture content in after the acid addition tank to be lower than the stoichiometric quantity of water that allows hydration of the total amount of the salt in the glycerin;

a high-temperature and high-pressure water treatment means for allowing high-temperature and high-pressure water to act on glycerin supplied from the acid addition tank, which is located downstream of the acid addition tank; and a precipitate removal means for separating and removing a precipitate in glycerin supplied from the acid addition tank and supplying the glycerin from which the precipitate has been removed to the supercritical water treatment means, the precipitate removal means being arranged downstream of the acid addition tank and upstream of the supercritical water treatment means, wherein the acid is an inorganic acid.

9. The device according to claim 8, which further comprises a water addition tank for adding water to glycerin from which the precipitate has been removed provided with a means for supplying the glycerin from the precipitate removal means, a means for supplying water, and an agitation means, the tank being arranged downstream of the precipitate removal means and upstream of the high-temperature and high-pressure water treatment means, and wherein glycerin to which water has been added in the water addition tank is supplied to the high-temperature and high-pressure water treatment means.

10. The method according to claim 1, wherein the alkali catalyst is sodium hydroxide, and the acid is sulfuric acid.

11. The method according to claim 3, wherein the alkali catalyst is sodium hydroxide, and the acid is sulfuric acid.

12. The device according to claim 6, wherein the acid is sulfuric acid.

13. The device according to claim 8, wherein the acid is sulfuric acid.

* * * * *